US005281612A

United States Patent [19]
Domagala et al.

[11] Patent Number: 5,281,612
[45] Date of Patent: Jan. 25, 1994

[54] NAPHTHYRIDINE ANTIBACTERIAL AGENTS

[75] Inventors: John M. Domagala, Canton; Thomas F. Mich; Jeffrey B. Nichols, both of Ann Arbor, all of Mich.

[73] Assignee: Warner-Lambert Company, Morris Plains, N.J.

[21] Appl. No.: 200,090

[22] Filed: May 27, 1988

Related U.S. Application Data

[60] Continuation-in-part of Ser. No. 907,340, Sep. 15, 1986, Pat. No. 4,777,175, which is a division of Ser. No. 764,357, Aug. 12, 1985, Pat. No. 4,638,067, which is a division of Ser. No. 692,820, Jan. 23, 1985, Pat. No. 4,665,079, which is a continuation-in-part of Ser. No. 581,157, Feb. 17, 1984, abandoned, which is a continuation-in-part of Ser. No. 522,275, Aug. 12, 1983, abandoned, which is a continuation-in-part of Ser. No. 416,406, Sep. 9, 1982, abandoned.

[51] Int. Cl.$^5$ ................. A61K 31/435; C07D 471/04
[52] U.S. Cl. .................................... 514/300; 546/123; 540/599; 514/210; 514/212
[58] Field of Search ............... 546/123; 514/300, 210, 514/212; 540/599

[56] References Cited

U.S. PATENT DOCUMENTS

| | | | |
|---|---|---|---|
| 3,590,036 | 6/1971 | Lesher et al. | |
| 3,849,421 | 11/1974 | Nakugome et al. | 546/123 |
| 3,876,650 | 4/1975 | Lesher et al. | |
| 3,963,736 | 6/1976 | Nakagome et al. | 260/295.5 |
| 4,382,937 | 5/1983 | Matsumoto et al. | 424/256 |
| 4,448,962 | 5/1984 | Irikura et al. | 544/362 |
| 4,477,449 | 10/1984 | Sanchez | 424/246 |
| 4,616,019 | 10/1986 | Chu | 514/254 |
| 4,620,007 | 10/1986 | Grohe et al. | 546/156 |
| 4,649,144 | 3/1987 | Matsumoto et al. | 514/300 |

FOREIGN PATENT DOCUMENTS

| | | |
|---|---|---|
| 0027752 | 4/1981 | European Pat. Off. |
| 0047005 | 3/1982 | European Pat. Off. |
| 0049355 | 4/1982 | European Pat. Off. |
| 0106489 | 4/1984 | European Pat. Off. |
| 0126355 | 11/1984 | European Pat. Off. |
| 0132845 | 2/1985 | European Pat. Off. |
| 2138003 | 5/1972 | France . |
| 2183895 | 5/1983 | France . |
| 956253 | 4/1964 | United Kingdom . |

OTHER PUBLICATIONS

EPO Search Report and related attachments for EP Applications 85301009.8 and 83305148.5, Feb. 19, 1985.

*Primary Examiner*—Glennon H. Hollrah
*Assistant Examiner*—Deborah Lambkin
*Attorney, Agent, or Firm*—Ronald A. Daignault; Elizabeth M. Anderson

[57] ABSTRACT

Novel naphthyridine-carboxylic acids as antibacterial agents are described as well as methods for their manufacture, formulation, and use in treating bacterial infections.

16 Claims, No Drawings

NAPHTHYRIDINE ANTIBACTERIAL AGENTS

CROSS REFERENCE TO RELATED APPLICATION

This application is a continuation-in-part of U.S. Ser. No. 907,340 of Sep. 15, 1986, now U.S. Pat. No. 4,777,175, which is a divisional of U.S. Ser. No. 764,357 of Aug. 12, 1985, now U.S. Pat. No. 4,638,067, which is a divisional of U.S. Ser. No. 692,820 of Jan. 23, 1985, now U.S. Pat. No. 4,665,079, which is a continuation-in-part of U.S. Ser. No. 581,157 of Feb. 17, 1984, now abandoned, which is a continuation-in-part of U.S. Ser. No. 522,275 of Aug. 12, 1983, now abandoned, and which is a continuation-in-part of U.S. Ser. No. 416,406 of Sep. 9, 1982, now abandoned.

BACKGROUND OF THE INVENTION

U.S. Pat. No. 4,341,784 discloses certain substituted 7-(3-amino-1-pyrrolidinyl)-1-ethyl-6-fluoro-1,4-dihydro-4-oxo-1,8-naphthyridine-3-carboxylic acids having the general formula:

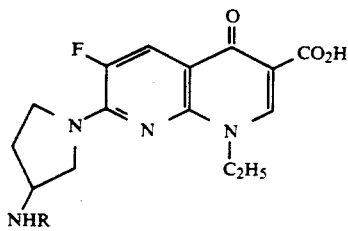

The compounds are disclosed to have antibacterial activity.

Certain 7-heterocyclic substituted 1,8-naphthyridines are disclosed in Eur. J. Med. Chem. - Chimica Therapeutica, 29, 27 (1977), as possessing antibacterial activity.

SUMMARY OF THE INVENTION

The invention in a first generic chemical compound aspect is a compound having the structural Formula I

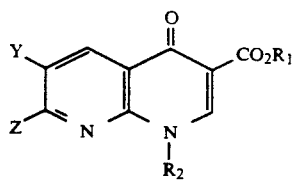

wherein Z is $-Z'\sim(CR_5R_6)_{n''}NR_3R_4$, in which $Z'$ is

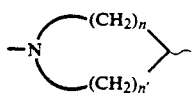

Y is hydrogen, fluorine, chlorine, or bromine; n is 1, 2, 3, or 4; n' is 1, 2, 3, or 4 wherein n+n' is a total of 2, 3, 4, or 5, and n" is 0, 1, or 2;

$R_1$ is hydrogen, alkyl having from one to six carbon atoms or a cation;

$R_2$ is alkyl having from one to four carbon atoms, vinyl, haloalkyl, or hydroxyalkyl having from two to four carbon atoms, or cycloalkyl having three to six carbon atoms; $R_3$ is hydrogen, alkyl having from one to four carbon atoms or cycloalkyl having three to six carbon atoms;

$R_4$ is hydrogen, alkyl from one to four carbon atoms, hydroxyalkyl having two to four carbon atoms, trifluoroethyl or $R_7CO-$ wherein $R_7$ is alkyl having from one to four carbon atoms, or alkoxy having from one to four carbon atoms, with the proviso that when $R_2$ is ethyl and Z is

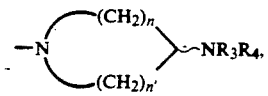

in which n+n' is 3, $R_3$ is cycloalkyl having three to six carbon atoms, or $R_3$ is alkyl from one to four carbon atoms and $R_4$ is alkyl from one to four carbon atoms, hydroxyalkyl having two to four carbon atoms or trifluoroethyl;

$R_5$ is hydrogen, or alkyl having from one to three carbon atoms;

$R_6$ is hydrogen or alkyl having from one to three carbon atoms, and the pharmaceutically acceptable acid addition or base salts thereof The significance of the symbol $\sim$ is intended only to show point of attachment of the radical to other atoms of the remaining component of the molecule.

Preferred compounds of this invention are those wherein Y is fluorine.

Other preferred compounds of this invention are those wherein $R_1$ is hydrogen or a pharmaceutically acceptable base salt such as metal or amine salt.

Other preferred compounds of this invention are those wherein $R_2$ is ethyl, vinyl, 2-fluoroethyl, or cyclopropyl.

Additionally, most preferred compounds include those of Formula I wherein Y is fluorine, $R_2$ is cyclopropyl; Z is

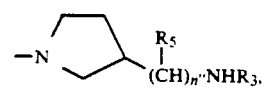

in which n" is 0 or 1; $R_5$ is hydrogen or methyl; $R_3$ is hydrogen, methyl, ethyl, 1- or 2-propyl, and $R_1$ is hydrogen or a pharmaceutically acceptable base salt thereof.

Particularly preferred species of the invention are the compounds having the names:

7-[3-(aminomethyl)-1-pyrrolidinyl]-1-ethyl-6-fluoro-1,4-dihydro-4-oxo-1,8-naphthyridine -3-carboxylic acid;

1-ethyl-7-[3-[(ethylamino)methyl]-1-pyrrolidinyl]-6-fluoro-1,4-dihydro-4-oxo-1,8 -naphthyridine-3-carboxylic acid;

7-[3-(aminomethyl)-1-pyrrolidinyl]-1-cyclopropyl-1,4-dihydro-6-fluoro-4-oxo-1,8 -naphthyridine-3-carboxylic acid;

1-cyclopropyl-7-[3-[(ethylamino)methyl]-1-pyrrolidinyl]-1,4-dihydro-6-fluoro-4-oxo-1,8 -naphthyridine-3-carboxylic acid;

7-[3-amino-1-pyrrolidinyl]-1-cyclopropyl-1,4-dihydro-6-fluoro-4-oxo-1,8 -naphthyridine-3-carboxylic acid;

1-ethyl-6-fluoro-1,4-dihydro-7-[3-[(methylamino)-methyl]-1-pyrrolidinyl]-4-oxo-1,8-naphthyridine-3-carboxylic acid;

7-[3-(2-propylamino)methyl]-1-pyrrolidinyl]-1-cyclopropyl-6-fluoro-1,4-dihydro-4-oxo-1,8-naphthyridine-3-carboxylic acid;

7-[3-[(propylamino)methyl]-1-pyrrolidinyl]-1-cyclopropyl-6-fluoro-1,4-dihydro-4-oxo-1,8-naphthyridine-3-carboxylic acid;

1-cyclopropyl-6-fluoro-1,4-dihydro-7-[3-[(methylamino)methyl]-1-pyrrolidinyl]-4-oxo-1,8,-naphthyridine-3-carboxylic acid;

7-[3-(1-aminoethyl)-1-pyrrolidinyl]-1-cyclopropyl-6-fluoro-1,4-dihydro-4-oxo-1,8-naphthyridine-3-carboxylic acid and its individual epimeric forms, and the pharmaceutically acceptable acid addition or base salts thereof.

The following process for preparing compounds of the formula

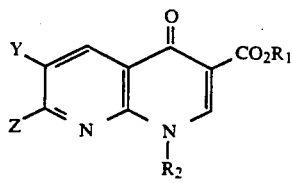

wherein $R_1$, $R_2$, Y, and Z are as defined for Formula I which comprises reacting a compound having the following structural formula

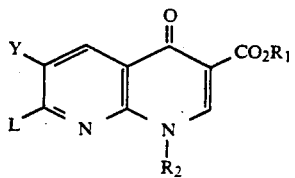

with an amine corresponding to the group Z wherein Z is the compound having the structural formula

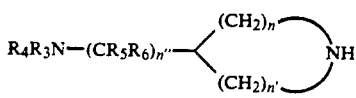

wherein all of the above terms are as defined in Formula I and L is a leaving group which is preferably fluorine or chlorine.

The invention also includes a pharmaceutical composition which comprises an antibacterially effective amount of a compound having structural Formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the invention having the structural Formula III may be readily prepared by treating a corresponding compound having the structural Formula IV with the desired cyclic amine For purposes of this reaction, the alkylamine substituent of Compound V may, if desired, be protected by a group which renders it substantially inert to the reaction conditions. Thus, for example, protecting groups such as the following may be utilized:

carboxylic acyl groups such as formyl, acetyl, trifluoroacetyl;

alkoxycarbonyl groups such as ethoxycarbonyl, t-butoxycarbonyl, $\beta,\beta,\beta$-trichloroethoxycarbonyl, $\beta$-iodoethoxycarbonyl;

aryloxycarbonyl groups such as benzyloxycarbonyl, p-methoxybenzyloxycarbonyl, phenoxycarbonyl; silyl groups such trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between Compound IV and Compound V, if desired, by procedures known to those skilled in the art. For example, the ethoxycarbonyl group may be removed by acid or base hydrolysis and the trityl group may be removed by hydrogenolysis.

The reaction between the compound of structural Formula IV and a suitably protected compound of Formula V may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of Formula V may be utilized as the acid acceptor.

Convenient solvents for this reaction are non-reactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group $R_4$ may be accomplished either before or after isolating the product, III. Alternatively, the protecting group $R_4$ need not be removed.

The starting compounds having structural Formula IV are known in the art or, if new, may be prepared from known starting materials by standard procedures or by variations thereof. Thus the following compounds are disclosed in the noted references:

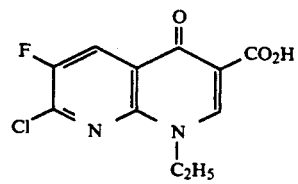

European Patent Application 80 40 1369

7-Chloro-1-cyclopropyl-6-fluoro-1,4-dihydro-4-oxo-1,8-naphthyridine-3-carboxylic acid may be prepared by a series of reactions starting from 4-(6-chloro-3-nitro-2-pyridinyl)-1-piperazinecarboxylic acid, ethyl ester. The intermediate, 1-cyclopropyl-6-fluoro-1,4-dihydro-4-oxo-7-(1-piperazinyl)-1,8-naphthyridine-3- carboxylic acid can be converted to the 7-hydroxy derivative with a mixture of nitric and sulfuric acids which is then replaced by chlorine by treatment with phosphorus oxychloride to give the desired intermediate. The synthesis of both of the above N-cyclopropyl intermediates is described in the Preparative Examples.

The compounds of the invention having structural Formula V are either known compounds or they may be prepared from known starting materials by standard procedures or by variations thereof. For example, 3-pyrrolidinemethanamines having the structural formula D

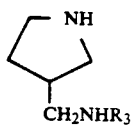

may be readily prepared from the known starting material methyl-5-oxo-1-(phenylmethyl)-3-pyrrolidinecarboxylate, A, [J. Org. Chem., 26, 1519 (1961)] by the following reaction sequence

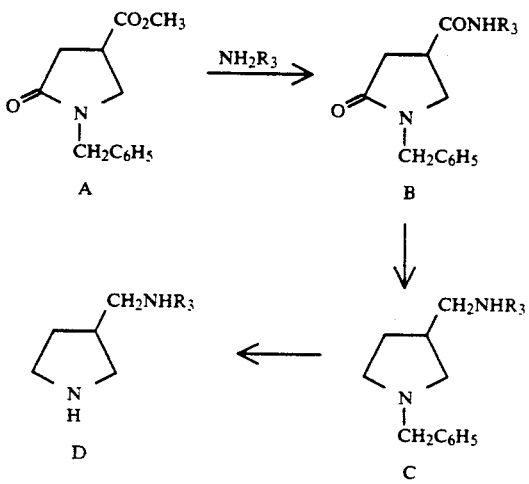

The compound wherein $R_3$ is hydrogen, namely 3-pyrrolidinemethanamine, has been reported in J. Org. Chem., 26, 4955 (1961).

Thus Compound A may be converted to the corresponding amide B by treatment with $R_3NH_2$; for example, a saturated solution of ethylamine in an alkanol such as methyl alcohol may be utilized. The diamide B may next be reduced to produce the corresponding diamine C. This reduction may be carried out using lithium aluminum hydride, for example, in a convenient solvent such as tetrahydrofuran. Compound C may next be debenzylated, for example using hydrogen and 20% palladium on carbon catalyst to produce the diamine D. Alternatively, when R=H in C, the primary amine function may be protected with a group $R_4$ as defined, hereinabove. For example, the primary amine function may be acylated with an acyl halide such as acetyl chloride by well-known procedures. The primary amine function of C may also be converted to a carbamate ester such as the ethyl ester by treatment with ethyl chloroformate in the presence of a strong base such as 1,8-diazabicyclo[5.4.0]undec-7-ene in a convenient solvent such as methylene chloride. The benzyl group may next be removed, for example, as described above for Compound C, thereby producing Compound D where R is —$CO_2ET$, which after conversion to a compound of the type V may be reacted with a compound having the structural Formula IV to thereby produce a corresponding compound having the structural Formula I. The —$CO_2Et$ group may be removed by standard procedures.

Starting materials of the invention having structural formula E

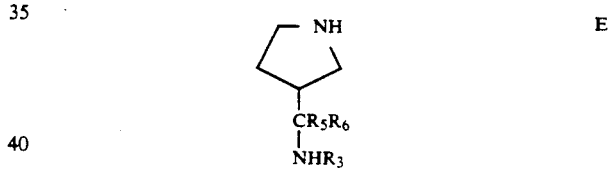

wherein at least one of $R_5$ or $R_6$ is alkyl as defined above, may be readily prepared also from the known starting material A, above, by the following reaction sequence.

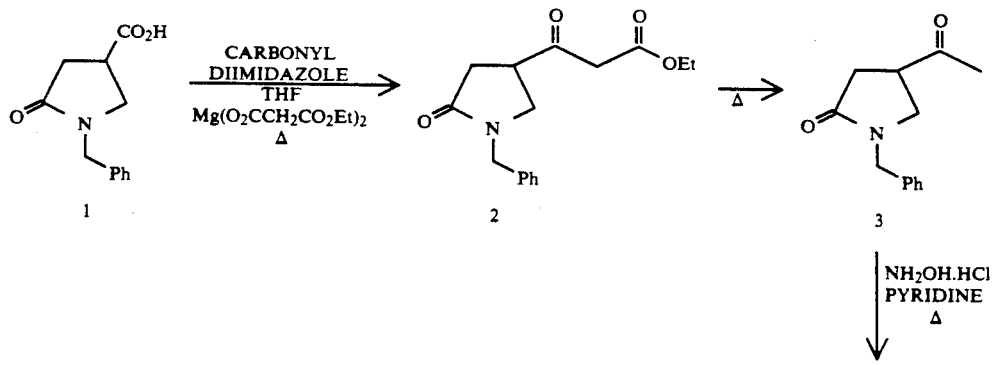

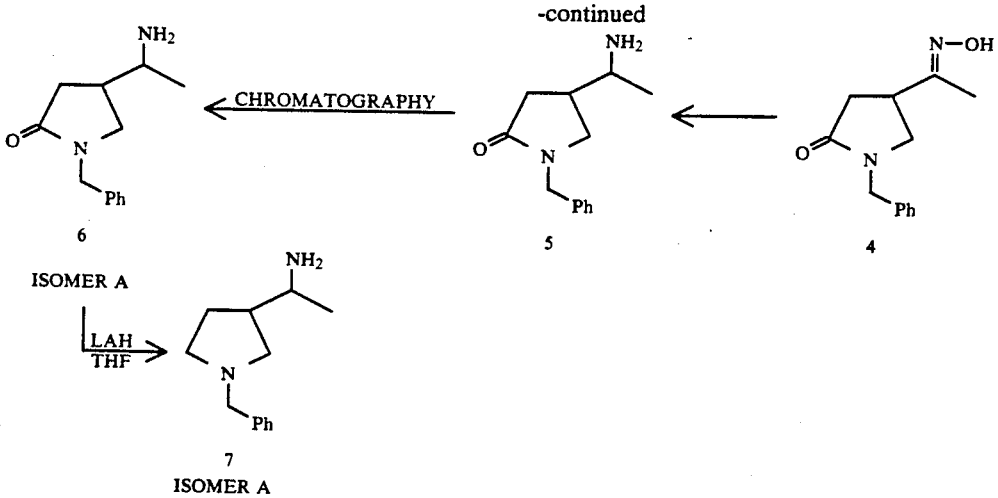

The pathway to the pyrrolidine E is illustrated here. The carboxylic acid 1 is converted to the β-keto ester by treatment with 1,1'-carbonyldiimidazole and magnesium bis-(ethylmalonate) and this is decarboxylated to give the 4-acetyl compound 3. This is then converted to the oxime and reduced with Raney nickel in methanolic ammonia to give amine 5. This compound is chromatographed to obtain the individual diastereomers and the faster moving of the two (here referred to as isomer A) is carried on. Lithium aluminum hydride reduction of 6 results in the formation of 3-(1-amino-ethyl)-1-benzyl-pyrrolidine. The 1-benzyl group may be ultimately removed by known methods, e.g., hydrogenolysis.

The compounds of the invention display antibacterial activity when tested by the microtitration dilution method as described in Heifetz, et al, Antimicr. Agents & Chemoth., 6, 124 (1974), which is incorporated herein by reference.

By use of the above referenced method, the followed minimum inhibitory concentration values (MICs in μg/mL) were obtained for representative compounds of the invention and the prior art compound 7-(3-amino-1-pyrrolidinyl)-1-ethyl-6-fluoro-1,4-dihydro-4-oxo-1,8-naphthyridine-3-carboxylic acid designated as ** in the table.

| Organisms | ** | Compound Ex. 1 | Compound Ex. 2 | Compound Ex. 3 | Compound Ex. 10 | Compound Ex. 11 |
|---|---|---|---|---|---|---|
| Enterobacter cloacae MA 2646 | 0.05 | 0.1 | 0.1 | 0.2 | 0.025 | 0.1 |
| Escherichia coli Vogel | 0.025 | 0.05 | 0.05 | 0.1 | 0.006 | 0.1 |
| Klebsiella pneumoniae MGH-2 | 0.1 | 0.1 | 0.1 | 0.2 | 0.013 | 0.1 |
| Proteus rettgeri M 1771 | 0.05 | 0.2 | 1.6 | 1.6 | 0.025 | 0.4 |
| Pseudomonas aeruginosa UI-18 | 0.1 | 0.1 | 0.4 | 1.6 | 0.05 | 0.2 |
| Staphylococcus aureus H 228 | 0.4 | 0.1 | 0.2 | 0.2 | 0.2 | 0.1 |
| Staphylococcus aureus UC-76 | 0.05 | 0.025 | 0.05 | 0.05 | 0.013 | 0.003 |
| Staphylococcus faecalis MGH-2 | 0.4 | 0.1 | 0.2 | 0.2 | 0.2 | 0.025 |
| Streptococcus pneumoniae SV-1 | 0.4 | 0.025 | 0.1 | 0.1 | 0.2 | 0.05 |
| Streptococcus pyogenes C-203 | 1.6 | 0.025 | 0.1 | 0.1 | 0.2 | 0.025 |

| Organisms | Compound Ex. 12 | Compound Ex. 12a | Compound Ex. 13 | Compound Ex. 14 | Compound Ex. 15 |
|---|---|---|---|---|---|
| Enterobacter cloacae MA 2646 | 0.2 | 0.2 | 0.1 | 0.2 | 0.025 |
| Escherichia coli Vogel | 0.05 | 0.1 | 0.1 | 0.2 | 0.025 |
| Klebsiella pneumoniae MGH-2 | 0.1 | 0.2 | 0.2 | 0.2 | 0.1 |
| Proteus rettgeri M 1771 | 0.8 | 0.4 | 1.6 | 0.8 | 0.2 |
| Pseudomonas aeruginosa UI-18 | 0.8 | 0.8 | 0.8 | 0.8 | 0.8 |
| Staphylococcus aureus H 228 | 0.1 | 0.2 | 0.2 | 0.4 | 0.05 |
| Staphylococcus aureus UC-76 | 0.05 | 0.025 | 0.1 | 0.2 | 0.006 |
| Staphylococcus faecalis MGH-2 | 0.1 | 0.2 | 0.2 | 0.4 | 0.05 |
| Streptococcus pneumoniae SV-1 | 0.1 | 0.025 | 0.2 | 0.1 | 0.006 |
| Streptococcus pyogenes C-203 | 0.1 | 0.05 | 0.2 | 0.2 | 0.013 |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Such heavy metal salts are effective in the treatment of burns especially when applied to the affected surface of a burn victim either directly or in combination with a physiologically acceptable carrier such as a water dispersible, hydrophilic carrier. Examples of suitable amines are N,N'dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R is hydrogen gives the corresponding basic salt.

The compounds of the invention can exist in unsolvated as well as solvated forms, including hydrated forms In general, the solvated forms, including hydrated forms and the like are equivalent to the unsolvated forms for purposes of the invention.

The alkyl groups contemplated by the invention comprise both straight and branched carbon chains of from one to about three carbon atoms except when specifically stated to be greater than three carbon atoms. Representative of such groups are methyl, ethyl, propyl, isopropyl, and the like.

The cycloalkyl groups contemplated by the invention comprise those having three to six carbons atoms such as cyclopropyl, cyclobutyl, cyclopentyl, and cyclohexyl.

The alkoxy groups contemplated by the invention comprise both straight and branched carbon chains of from one to about six carbon atoms unless otherwise specified. Representative of such groups are methoxy, ethoxy, propoxy, i-propoxy, t-butoxy, hexoxy, and the like.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are $\beta$-fluoroethyl, $\beta$-chloroethyl, $\beta$, $\beta$-dichloroethyl, $\beta$-chloropropyl, $\beta$-chloro-2-propyl, $\gamma$-iodobutyl, and the like.

The term halogen is intended to include fluorine, chlorine, bromine, and iodine unless otherwise specified.

Certain compounds of the invention may exist in optically active forms. The pure D isomer, pure L isomer as well as mixtures thereof; including the racemic mixtures, are contemplated by the invention. Additional asymmetric carbon atoms may be present in a substituent such as an alkyl group. All such isomers as well as mixtures thereof are intended to be included in the invention.

The compounds of the invention can be prepared and administered in a wide variety of oral, parenteral and topical dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of Formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the Package containing discrete quantities of preparation, for example, packeted tablets, capsules, powders in vials or ampoules, and ointments in tubes or jars. The unit dosage form can also be a capsule, cachet, tablet, gel or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

7-[3-(Aminomethyl)-1-pyrrolidinyl]-1-ethyl-6-fluoro-1,4-dihydro-4-oxo-1,8-naphthyridine -3-carboxylic Acid A mixture of 2 00 g (7.39 mmole) of 7-chloro-1-ethyl-6-fluoro-1,4-dihydro-4-oxo-1,8 -napthyridine-3-carboxylic acid, 250 mL acetonitrile and 2.22 g (22.17 mmole) 3-pyrrolidinemethanamine [J. Org. Chem., 26, 4955 (1961)], was stirred at room temperature for four days. The reaction was filtered and the precipitate dissolved in 500 mL ammonium hydroxide at pH 10.5. This solution was filtered and the solvent removed at reduced pressure. The product was washed in 2×10 mL of water, then with ethanol/ether (1:1) until dry to give 1.65 g of 7-[3-(aminomethyl)-1-pyrrolidinyl]-1-ethyl-6-fluoro-1,4-dihydro-4-oxo -1,8-naphthyridine-3-carboxylic acid, mp 217°–218.5° C. Analysis calculated for $C_{16}H_{19}FN_4O_3.1/2H_2O$:

C, 55.97; H, 5.87; N, 16.32
Found C, 55.89; H, 5.66; N, 16.33,

EXAMPLE 2

1-Ethyl-6-fluoro-1,4-dihydro-7-[3-[(methylamino)methyl]-1-pyrrolidinyl]-4-oxo-1,8-naphthyridine-3-carboxylic Acid 1.00 g (3.69 mmole) 7-chloro-1-ethyl-6-fluoro-1,4-dihydro-4-oxo-1,8-napthyridine-3 -carboxylic acid, 40 mL acetonitrile, and 1.27 g (11.08 mmole) N-methyl-3-pyrrolidinemethanamine are stirred at room temperature for three days. The reaction was filtered and the precipitate dissolved in aqueous ammonium hydroxide at pH 11. The solution was filtered and the solvent removed at reduced pressure. The product was washed with 5 mL of water, 10 mL ethanol/ether (1:1), and finally with ether until dry to give 0.571 g of 1-ethyl-6-fluoro-1,4-dihydro-7-[3-[(methylamino)methyl -1-pyrrolidinyl]-4-oxo-1,8-naphthyridine-3-carboxylic acid, mp 251°–253° C.

Analysis calculated for $C_{17}H_{21}FN_4O_3.1/2H_2O$:
C, 57.13; H, 6.20; N, 15.68,
Found C, 57.19; H, 6.03; N, 15.85,

EXAMPLE 3

1-Ethyl-7-[3-[(ethylamino)methyl]-1-pyrrolidinyl]-6-fluoro-1,4-dihydro-4-oxo-1,8 -naphthyridine-3-carboxylic Acid 1 00 g (3.69 mmole) of 7-chloro-1-ethyl-6-fluoro-1,4-dihydro-4-oxo-1,8-napthyridine-3 -carboxylic acid, 100 mL acetonitrile and 1.42 g (11.08 mmole) of N-ethyl-3-pyrrolidinemethanamine were stirred for three days at room temperature. The reaction mixture was then filtered, and the precipitate washed with water, ethanol/ether (1:3), and finally with ether until dry to give 0 715 g of 1-ethyl-7-[3-[(ethylamino)-methyl]-1-pyrrolidinyl]-6-fluoro-1,4 -dihydro-4-oxo-1,8-napthyridine-3-carboxylic acid, mp 229.5°–231.5° C.

The analysis was calculated for $C_{18}H_{23}FN_4O_3.0.24-H_2O$;

C, 58.94; H, 6 45; N, 15.27; $H_2O$, 1.20.
Found C, 58.28; H, 6.85; N, 14.90; $H_2O$, 0.80.

EXAMPLE 4

1-Ethyl-6-fluoro-1,4-dihydro-4-oxo-7-[3-[(propylamino)methyl]-1-pyrrolidinyl]-1,8 -naphthyridine-3-carboxylic Acid A near solution of 0.82 g (3.0 mmole) of 7-chloro-1-ethyl-6-fluoro-1,4-dihydro-4-oxo-1,8 -naphthyridine-3-carboxylic acid and 1.4 g (10 mmole) of N-propyl-3-pyrrolidinemethanamine in 50 mL of acetonitrile was heated at reflux for four hours. The solvent was removed in vacuo, the residue dissolved in water, filtered through a fiber glass pad to clarify and the filtrate adjusted to pH 1.8 with 6M hydrochloric acid. The resulting clear solution was lyophilized and the residue recrystallized from ethanol to give 400 mg 1-ethyl-6-fluoro-1,4-dihydro-4-oxo-7-[3-(propylamino)methyl]-1-pyrrolidinyl]-1,8 -naphthyridine-3-carboxylic acid, mp 281°–283° C. as the hydrochloride.

EXAMPLE 5

1-Ethyl-6-fluoro-1,4-dihydro-7-[3-[(1-methylethyl)amino]methyl]-1-pyrrolidinyl]-4 -oxo-1,8-naphthyridine-3-carboxylic Acid A near solution of 0.82 g (3.0 mmole) of 7-chloro-1-ethyl-6-fluoro-1,4-dihydro-4-oxo-1,8 -naphthyridine-3-carboxylic acid and 1.4 g (10 mmole) of N-(2-propyl)-3-pyrrolidinemethanamine in 50 mL of acetonitrile was heated at reflux for one hour. The solvent was removed in vacuo, the residue dissolved in water, filtered through a fiber glass pad to clarify and the filtrate adjusted to pH 2.0 with 6M hydrochloric acid. The resulting clear solution was lyophilized and the residue recrystallized from ethanol to give 200 mg of 1-ethyl-6-fluoro-1,4-dihydro-7-[3-[[(1 -methylethyl)amino]methyl]-1-pyrrolidinyl]-4-oxo-1,8-naphthyridine-3-carboxylic acid, mp 302°–304° C. as the hydrochloride.

EXAMPLE 6

7-[3-[(Cyclopropylaminomethyl]-1-pyrrolidinyl]-1-ethyl-6-fluoro-1,4-dihydro-4-oxo-1,8 -naphthyridine-3-carboxylic Acid A near solution of 0.82 g (3.0 mmole) of 7-chloro-1-ethyl-6-fluoro-1,4-dihydro-4-oxo-1,8-naphthyridine-3-carboxylic acid and 1.4 g (10 mmole) of cyclopropyl-3-pyrrolidinemethanamine in 50 mL of acetonitrile was heated at reflux for two hours. The solvent was removed in vacuo, the residue dissolved in water, filtered through a fiber glass pad to clarify and the filtrate adjusted to pH 2.0 with 6M hydrochloric acid. The resulting clear solution was lyophilized and the residue recrystallized from ethanol to give 600 mg of 7-[3-[(cyclopropylamino)methyl]-1-pyrrolidinyl]-1-ethyl-6-fluoro-1,4-dihydro-4-oxo-1,8-naphthyridine-3-carboxylic acid, mp 271°-274° C. as the hydrochloride.

EXAMPLE 7

7-[4-(Aminomethyl)-1-piperidinyl]-1-ethyl-6-fluoro-1,4-dihydro-4-oxo-1,8-naphthyridine-3-carboxylic Acid A mixture of 0.52 g (0.19 mmole) of 7-chloro-1-ethyl-6-fluoro-1,4-dihydro-4-oxo-1,8-naphthyridine-3-carboxylic acid, 150 mL acetonitrile, and 0.66 g (5.76 mmole) 4-aminomethylpiperidine [J. Med. Chem., 9 441 (1966)] was stirred at room temperature for four days. The reaction was filtered and the precipitate dissolved in 500 mL of aqueous ammonium hydroxide at pH 10.5. The solution was filtered and the solvent was removed at reduced pressure. The precipitate was washed with 5 mL of water, then ether until dry to give 0.42 g of 7-[4-(aminomethyl)-1-piperidinyl]-1-ethyl-6-fluoro-1,4-dihydro-4-oxo-1,8-naphthyridine-3-carboxylic acid, mp 203°-206° C.

Analysis for $C_{17}H_{21}FN_4O_3 \cdot H_2O$;
C, 55.73; H, 6.33; N, 15.29.
Found C, 55.30; H, 6.03; N, 15.30.

EXAMPLE 8

7-[3-(Aminomethyl)-1-piperidinyl]-1-ethyl-6-fluoro-1,4-dihydro-4-oxo-1,8-naphthyridine-3-carboxylic Acid A mixture of 1.04 g (3.84 mmole) of 7-chloro-1-ethyl-6-fluoro-1,4-dihydro-4-oxo-1,8-naphthyridine-3-carboxylic acid, 100 mL of acetonitrile and 1.32 g (11.5 mmole) of 3-aminomethylpiperidine [J. Org. Chem., 44, 4536 (1979)] was stirred at room temperature for four days. The reaction was filtered and the precipitate dissolved in aqueous ammonia, pH 10.5. The solution was filtered and the solvent removed at reduced pressure. The product was washed with water, then ether until dry to give 1 23 g of 7-[3-(aminomethyl)-1-piperidinyl]-1-ethyl-6-fluoro-1,4-dihydro-4-oxo-1,8-naphthyridine-3-carboxylic acid, mp 120°-122° C.

Analysis for $C_{17}H_{21}FN_4O_3 \cdot 3H_2O$;
C, 57.72; H, 6.15; N, 16.08.
Found C, 57.72; H, 6.00; N, 15.80.

EXAMPLE 9

1-Ethyl-6-fluoro-1,4-dihydro-7-[3-[(methylamino)methyl]-1-azetidinyl]-4-oxo-1,8-naphthyridine-3-carboxylic Acid A suspension of 0.81 g (3.0 mmole) of 7-chloro-1-ethyl-6-fluoro-1,4-dihydro-4-oxo-1,8-naphthyridine-3-carboxylic acid, 0.9 g (9.0 mmole) of N-methyl-3-azetidinemethanamine and 30 mL of acetonitrile was refluxed for six hours. The reaction was cooled to 5° C. The filtered solids were washed with acetonitrile, ether, and dried in vacuo. The dried solid was suspended in 70 mL of water and made basic to pH 11.0 after filtering through a fiber glass pad to clarify, the filtrate was acidified to pH 7.4 with 1.0M hydrochloric acid. The resulting precipitate was removed by filtration, washed successively with water, 2-propanol, ether and dried in vacuo to give 270 mg of 1-ethyl-6-fluoro-1,4-dihydro-7-[3-[(methylamino)methyl]-1-azetidinyl]-4-oxo-1,8-naphthyridine-3-carboxylic acid, mp 180°-182° C.

Using N-ethyl-3-azetidinemethanamine in the above procedure gave 1-ethyl-7[(3-ethylaminomethyl)-1-azetidinyl]-6-fluoro-1,4-dihydro-4-oxo-1,8-naphthyridine-3-carboxylic acid, mp 208°-210° C. (9a).

EXAMPLE 10

7-[(3-Amino-1-pyrrolidinyl]-1-cyclopropyl-6-fluoro-1,4-dihydro-4-oxo-1,8-naphthyridine-3-carboxylic Acid A suspension of 5.65 g (20 mmole) of 7-chloro-1-cyclopropyl-6-fluoro-1,4-dihydro-4-oxo-1,8-naphthyridine-3-carboxylic acid, 4.65 g (25 mmole) of 3-t-butoxycarbonylaminopyrrolidine, 7.9 g (50 mmole) of 1,8-diazabicyclo[5.4.0]undec-7-ene and 150 mL of acetonitrile was stirred at 60° C. for one hour. The solvent was removed in vacuo and the residue was dissolved in 100 mL of trifluoroacetic acid. After stirring at room temperature for one hour, the solvent was removed in vacuo and the residue was suspended in water and the pH adjusted to 11.5 with 50% sodium hydroxide. After filtering through a fiberglass pad to clarify, the filtrate was acidified to 6.6 with 6M hydrochloric acid. The resulting precipitate was removed by filtration, washed with water, 2-propanol, ether, and dried in vacuo to give 6.5 g (98%) of the title compound, mp 284°-286° C.

EXAMPLE 11

7-[(3-Aminomethyl)-1-pyrrolidinyl]-1-cyclopropyl-6-fluoro-1,4-dihydro-4-oxo-1,8-naphthyridine-3-carboxylic Acid A suspension of 5.1 g (18 mmole) of 7-chloro-1-cyclopropyl-6-fluoro-1,4-dihydro-4-oxo-1,8-naphthyridine-3-carboxylic acid, 2.0 g (20 mmole) of 3-aminomethylpyrrolidine, 5.5 g (36 mmole) of 1,8-diazabicyclo[5.4.0]undec-7-ene and 125 mL of acetonitrile was stirred at room temperature for three hours. The precipitate was removed by filtration, washed with acetonitrile, and dried in vacuo to give 4.35 g (70%) of the title compound, mp 210°-212° C.

EXAMPLE 12

7-[3-(Ethylamino)methyl]-1-pyrrolidinyl]-1-cyclopropyl-6-fluoro-1,4-dihydro-4-oxo-1,8-naphthyridine-3-carboxylic Acid A suspension of 5.7 g (20 mmole) of 7-chloro-1-cyclopropyl-6-fluoro-1,4-dihydro-4-oxo-1,8-naphthyridine-3-carboxylic acid, 10.3 (80 mmole) of 3-ethylaminomethylpyrrolidine and 125 mL of acetonitrile was stirred at room temperature for 0.5 hours after an initial exotherm (60° C.). The solid was removed by filtration, washed with acetonitrile, and dried in vacuo to give 6.0 g (80%) of the title compound, mp 268°-270° C.

In identical fashion the 1-cyclopropyl-6-fluoro-1,4-dihydro-7-[3-[(methylamino)methyl]-1-pyrrolidinyl]-4-oxo-1,8-naphthyridine-3-carboxylic acid, 12a, and the 7-[3-[(dimethylamino)methyl]-1-pyrrolidinyl]-1-cyclopropyl-6-fluoro-1,4-dihydro-4-oxo-1,8-naphthyridine-3-carboxylic acid, 12b, were prepared.

EXAMPLE 13

7-[3-[(2-Propylamino)methyl]-1-pyrrolidinyl]-1-cyclopropyl-6-fluoro-1,4-dihydro-4-oxo-1,8-naphthyridine-3-carboxylic Acid A suspension of 1.13 g (3.0 mmole) of 7-chloro-1-cyclopropyl-6-fluoro-1,4-dihydro-4-oxo-1,8-naphthyridine-3-carboxylic acid, 0.63 g (4.4 mmole) of 3-[(2- propyl)aminomethyl]pyrrolidine, 1.22 g (8.0 mmole) of 1,8-diazabicyclo[5.4.0]undec-7-ene and 30 mL of acetonitrile was stirred at room temperature for two hours. The precipitate was removed by filtration, washed with acetonitrile, and dried in vacuo to give 1.3 g (84%) of the title compound, mp 240°-243° C.

EXAMPLE 14

7-[3-[(Propylamino)methyl]-1-pyrrolidinyl]-1-cyclopropyl-6-fluoro-1,4-dihydro-4-oxo-1, 8,-naphthyridine-3-carboxylic Acid A suspension of 1.13 g (4.0 mmole) of 7-chloro-1-cyclopropyl-6-fluoro-1,4-dihydro-4-oxo-1,8 -naphthyridine-3-carboxylic acid, 0.63 g (4.4 mmole) of 3-[(propylamino)methyl]pyrrolidine, 1.22 g (8.0 mmole) of 1,8-diazabicyclo[5.4.0]undec-7-ene and 30 mL of acetonitrile was stirred at room temperature for 2.5 hours. The precipitate was removed by filtration, washed with acetonitrile and dried in vacuo to give 1.15 g (74%) of the title compound, mp 230°-233° C.

EXAMPLE 15

7-[3-(1-Aminoethyl)-1-pyrrolidinyl]-1-cyclopropyl-6-fluoro-1,4-dihydro-4-oxo-1,8 -naphthyridine-3-carboxylic Acid Isomer A A mixture of 7-chloro-1-cyclopropyl-6-fluoro-1,4-dihydro-4-oxo-1,8-naphthyridine-3-carboxylic acid (0.48 g, 0.0017 mole), 3-[1-(N-tert-butoxycarbonylamino)ethyl]pyrrolidine isomer A (0.49 g, 0.0021 mole) and triethylamine (0.85 mL, 0.006 mole) in acetonitrile (20 mL) was stirred at room temperature under nitrogen for 16 hours. After 30 minutes reaction had completely solidified. A white solid was filtered off, washed with acetonitrile, and carried on as is in the next step.

7-[3-(1-(N-tert-butoxycarbonylamino)ethyl)-1-pyrrolidinyl]-1-cyclopropyl-6-fluoro-1,4 -dihydro-4-oxo-1,8-naphthyridine-3-carboxylic acid isomer A (0.78 g, 0.0017 mole), preformed above, in ethanol (37 mL)/1N HCl (15 mL) was heated at 90° for 75 minutes. The reaction was cooled to room temperature and the solvent partially removed under reduced pressure. On standing a solid formed. This was filtered, washed with ethanol/diethyl ether, and then with diethyl ether and was dried in an oven under vacuum at 70° for two hours to give 7-[3-(1-aminoethyl)-1-pyrrolidinyl]-1-cyclopropyl-6-fluoro-1,4-dihydro-4-oxo-1,8 -naphthyridine-3-carboxylic acid isomer A (0.40 g, 57%) as a white powder, mp 322°-325° (dec).

NMR δ (TFA) 9.11 (1H,s), 8.06 (1H,d), 4.28-4.59 (2H,m) 3.73-4.09 (4H,m), 2.79-2.87 (1H,m), 2.37-2.47 (1H,m) 1.61 (3H,d), 1.49-1.56 (2H,d), 1.23 (2H,m).

EXAMPLE 16

7-[3-(1-Aminoethyl)-1-pvrrolidinyl]-1-cyclopropyl-6-fluoro-1,4-dihydro-4-oxo-1,8 -naphthyridine-3-carboxylic Acid Isomer B 7-Chloro-1-cyclopropyl-6-fluoro-1,4-dihydro-4 -oxo-1,8-naphthyridine-3-carboxylic acid (0.45 g, 0.0016 mole), 3-[1-(N-tert-butoxycarbonylamino)ethyl]-pyrrolidine isomer B (0.45 g, 0.002 mole) and triethylamine (0.8 mL, 0.006 mole) in acetonitrile (20 mL) were stirred at room temperature under nitrogen two hours and then heated at reflux 16 hours. The reaction was cooled to room temperature and the solvent removed under reduced pressure to give 1.19 g gold semisolid, which was carried on as is in the next step.

7-[3-(1-[N-tert-butoxycarbonylamino]ethyl)-1-pyrrolidinyl]-1-cyclopropyl-6-fluoro-1,4 -dihydro-4-oxo-1,8-naphthyridine-3-carboxylic acid isomer B (0.74 g, 0.0016 mole) in ethanol (35 mL)/1N HCl (14 mL) was heated at 90° for two hours. The reaction was cooled to room temperature and the solvent was removed under reduced pressure. The residue was treated with isopropyl alcohol twice and the solvent was removed under reduced pressure. The solid was dried in an oven under vacuum at 70° for 60 hours. The solid was then stirred up in water, filtered, and the filtrate was placed on a freeze drying apparatus for 16 hours. 7-[3-(1-aminoethyl)-1-pyrrolidinyl]-1-cyclopropyl-6-fluoro-1,4-dihydro-4-oxo-1,8 -naphthyridine-3-carboxylic acid isomer B was obtained (0.63 g, 80%) as a pale yellow solid, mp 281°-284° (dec).

PREPARATION OF STARTING MATERIALS

Example A

N-methyl-3-pyrrolidinemethanamine

N methyl-5-oxo-1-(phenylmethyl)-3-pyrrolidinecarboxamide

A mixture of 100 g (0.43 mole) of methyl 5-oxo-1-(phenylmethyl)pyrrolidinecarboxylate [J. Org. Chem., 26, 1519 (1961)], 500 mL methanol and 100 g (3.2 m ole) of methylamine was heated at 100° C. in a pressure reactor for 16 hours. The reaction mixture was cooled and the ammonia and methanol were removed under reduced pressure. The residue was taken up in dichloromethane and washed 3×100 mL 1N sodium hydroxide. The organic layer was dried over magnesium sulfate and the solvent removed at reduced pressure to give 88.3 g of N-methyl-5-oxo-1-(phenylmethyl)-3-pyrrolidinecarboxamide as a white solid, mp 82.5°-83.0° C.

Analysis calculated for $C_{13}H_{16}N_2O_2$:

C, 67.22; H, 6.94; N, 12.06 Found C, 66.98; H, 6.69; N, 12.02.

This material was used in the next step.

N-methyl-1-(phenylmethyl)-3-pyrrolidinemethanamine

To a suspension of 37.40 g (1.00 mole) lithium aluminum hydride in 1000 mL tetrahydrofuran, was added a solution of 88.3 g (0.380 mole) of N-methyl-5-oxo-1-(phenylmethyl)-3-pyrrolidinecarboxamide in tetrahydrofuran dropwise under nitrogen. The reaction was then refluxed overnight. The reaction flask was cooled in an ice bath and treated dropwise successively with 37.4 mL of water, 37.4 mL of 15% sodium hydroxide and 112.2 mL of water. The precipitated solids were filtered and washed with hot ethanol. The combined filtrates were concentrated, then dissolved in dichloromethane, filtered, dried over magnesium sulfate, and the solvent evaporated under reduced pressure to give 68.68 g of N-methyl-1-(phenylmethyl)-3-pyrrolidinemethanamine as an oil. This material was used without further purification in the step.

N-methyl-3-pyrrolidinemethanamine

A mixture of 67.28 g (0.32 mole) of N-methyl-1-(phenylmethyl)-3-pyrrolidinemethanamine, 3 g of 20% palladium on carbon, and 600 mL of methanol was shaken in an atmosphere of hydrogen at about $4.5 \times 10^5$ Pa at room temperature for 18 hours. Another 3 g of 20% palladium on carbon was added and the hydrogenation continued for 6.5 hours. Another 3.0 g of 20% palladium on charcoal was added and the hydrogenation continued for another 4.5 hours. The catalyst was filtered and the filtrate evaporated under reduced pressure. The residue was distilled under vacuum (72°–76° C., 10.5 mm Hg) to give 8.32 g N-methyl-3-pyrrolidinemethanamine.

Example B

N-Ethyl-5-oxo-1-(phenylmethyl)-3-pyrrolidinecarboxamide

A mixture of 200 g (0.86 mole) of methyl 5-oxo-1-(phenylmethyl)pyrrolidinecarboxylate [J. Org. Chem., 26, 1519 (1961)], 1000 mL methanol and 200 g (4.4 mole) of ethylamine was heated at 100° C. in a pressure reactor for 17.2 hours. The reaction mixture was cooled and the excess ethylamine and methanol were removed under reduced pressure. The residue was taken up in dichloromethane and washed 3×150 mL with 1N sodium hydroxide. The organic layer was dried over magnesium sulfate and the solvent removed at reduced pressure to give 104.6 g of N-ethyl-5-oxo-1-(phenylmethyl)-3-pyrrolidinecarboxamide as a white solid, mp 97°–99° C.

This material was used in the next step.

N-ethyl-1-(phenylmethyl)-3-pyrrolidinemethanamine

To a suspension of 108.68 g (2.860 mole) lithium aluminum hydride in 800 mL tetrahydrofuran, was added a solution of 194.5 g (0.790 mole) of N-ethyl-5-oxo-1-(phenylmethyl)-3-pyrrolidinecarboxamide in 600 mL tetrahydrofuran, dropwise under nitrogen. The reaction mixture was then refluxed four hours The reaction flask was cooled in an ice bath and treated dropwise successively with 108 mL of water, 108 mL of 15% sodium hydroxide, and 324 mL of water. The precipitated solids were filtered and washed with hot ethanol. The combined filtrates were concentrated, then dissolved in dichloromethane, filtered, dried over magnesium sulfate, and the solvent evaporated under reduced pressure to give 151.9 g of N-ethyl-1-(phenylmethyl)-3-pyrrolidinemethanamine as an oil.

This material was used without further purification in the next step.

N-ethyl-3-pyrrolidinemethanamine

A mixture of 151.65 g (0.695 mole) of N-ethyl-1-(phenylmethyl)-3-pyrrolidinemethanamine, 5 g of 20% palladium on carbon, and 1100 mL of ethanol was shaken in an atmosphere of hydrogen at about 4.5×10$^5$ Pa at room temperature for 21.6 hours. Another 5 g of 20% palladium on carbon was added and the hydrogenation continued for 24 hours. The catalyst was filtered and the filtrate evaporated under reduced pressure. The residue was distilled under vacuum (88°–91° C., 11.5 mm Hg) to give 66.0 g N-ethyl-3-pyrrolidinemethanamine.

Example C

N-Propyl-3-pyrrolidinemethanamine

5-Oxo-1-(phenylmethyl)-N-propyl-3-pyrrolidinecarboxamide

To a solution of 10.96 g (50 mmole) of 5-oxo-1-(phenylmethyl)-3-pyrrolidinecarboxylic acid in 150 mL of acetonitrile was added 9.73 g (60 mmole) of 1,1'-carbonyldiimidazole. The reaction was heated to 60° C. for one hour, cooled to room temperature and treated with 4.13 g (70 mmole) of n-propylamine. After stirring for two hours, the solvent was removed in vacuo and the residue partitioned between ether and water. The organic layer was washed with water, 1N hydrochloric acid, dried over magnesium sulfate, filtered, and evaporated in vacuo to give 12.0 g of 5-oxo-1-(phenylmethyl)-N-propyl-3-pyrrolidinecarboxamide, mp 86°–87° C.

1-(Phenylmethyl)-N-propyl-3-pyrrolidinemethanamine

To a suspension of 8.2 g (0.2 mole) of lithium aluminum hydride in 150 mL of dry tetrahydrofuran was added portionwise, 12.0 g (45.6 mmole) of solid 5-oxo-1-(phenylmethyl)-N-propyl-3-pyrrolidinecarboxamide. When the addition was complete, the reaction mixture was stirred at room temperature for 18 hours and then at reflux for two hours. After cooling to room temperature, the mixture was treated dropwise, successively, with 8 mL of water, 8 mL of 15% aqueous sodium hydroxide and 24 mL of water, titrating the final addition to produce a granular precipitate. The solid was removed by filtration, washed with tetrahydrofuran and the filtrate evaporated in vacuo to give 9.6 g of 1-(phenylmethyl)-N-propyl-3-pyrrolidinemethanamine, as a heavy syrup.

This material was used for the next step without further purification.

N-Propyl-3-pyrrolidinemethanamine

A mixture of 14.0 g (60.0 mmole) of 1-(phenylmethyl)-N-prop-yl-3-pyrrolidinemethanamine, 1.0 g of 20% palladium on carbon and 140 mL of methanol was shaken in an atmosphere of hydrogen at about 4.5×10$^5$ Pa at room temperature for 24 hours. The catalyst was removed by filtering through Celite, the filtrate concentrated and distilled in vacuo to give 7.1 g of N-propyl-3-pyrrolidinemethanamine, bp 49°–50° C./0.25 mm.

Example D

N-Cyclopropyl-3-pyrrolidinemethanamine

5-Oxo-1-(phenylmethyl)-N-cyclopropyl-3-pyrrolidinecarboxamide

To a solution of 16.4 g (75 mmole) of 5-oxo-1-(phenylmethyl)-3-pyrrolidinecarboxylic acid in 150 mL of acetonitrile was added 13.8 g (85 mmole) of 1,1'-carbonyldiimidazole. The reaction was heated to 60° C. for one hour, cooled to room temperature and treated with 4.85 g (85 mmole) of cyclopropylamine. The reaction was stirred at room temperature for 18 hours, the solvent removed in vacuo and the residue partitioned between chloroform and water. The organic layer was washed with water, 1N hydrochloric acid, dried over magnesium sulfate, filtered, and evaporated in vacuo to give 18.3 g of 5-oxo-1-(phenylmethyl)-N-cyclopropyl-3-pyrrolidinecarboxamide, mp 94°–96° C.

1-(Phenylmethyl)-N-cyclopropyl-3-pyrrolidinemethanamine

To a suspension of 8.2 g (0.20 mole) of lithium aluminum hydride in 150 mL of dry tetrahydrofuran was added portionwise 18.0 g (70.0 mmole) of solid 5-oxo-1-(phenylmethyl)-N-cyclopropyl-3-pyrrolidinecarboxamide. When the addition was complete, the reaction mixture was stirred at room temperature for 18 hours and then at reflux for two hours. After cooling to room temperature, the mixture was treated dropwise, successively, with 8 mL of water, 8 mL of 15% aqueous sodium hydroxide and 24 mL of water, titrating the final addition to produce a granular precipitate. The solid was removed by filtration, washed with tetrahydrofuran and the filtrate evaporated in vacuo to give 16.0 g of 1-(phenylmethyl)-N-cyclopropyl-3-pyrrolidinemethanamine, as a heavy oil. This was used for the next step without further purification.

N-Cyclopropyl-3-pyrrolidinemethanamine

A mixture of 13.6 g (59.0 mmole) of 1-(phenylmethyl)-N-cyclopropyl-3-pyrrolidinemethanamine, 0.5 g of 20% palladium on carbon and 140 mL of methanol was shaken in an atmosphere of hydrogen at about $4.5 \times 10^5$ Pa at room temperature for 24 hours. The catalyst was removed by filtering through Celite, the filtrate concentrated and distilled in vacuo to give 6.3 g of N-cyclopropyl-3-pyrrolidinemethanamine, bp 88°–90°/13 mm.

Example E

N-(2-Propyl)-3-pyrrolidinemethanamine

5-Oxo-1-(phenylmethyl)-N-(2-propyl)-3-pyrrolidinecarboxamide

To a solution of 16.4 g (75.0 mmole) of 5-oxo-1-(phenylmethyl)-3-pyrrolidinecarboxylic acid in 150 mL of acetonitrile was added 13.8 g (85.0 mmole) of 1,1'-carbonyldiimidazole. The reaction was heated to 60° C. for one hour, cooled to room temperature and treated with 5.0 g (85 mmole) of isopropylamine. The reaction was stirred at room temperature for 18 hours, the solvent removed in vacuo and the residue partitioned between chloroform and water. The organic layer was washed with water, 1N hydrochloric acid, dried over magnesium sulfate and evaporated in vacuo to give 18.6 g of 5-oxo-1-(phenylmethyl)-N-(2-propyl)-3-pyrrolidinecarboxamide, mp 122°–124° C.

1-(Phenylmethyl)-N-(2-propyl)-3-pyrrolidinemethanamine

To a suspension of 8.2 g (0.2 mole) of lithium aluminum hydride in 150 mL of dry tetrahydrofuran was added portionwise, 18.3 g (70.0 mmole) of solid 5-oxo-1-(phenylmethyl)-N-(2-propyl)-3 -pyrrolidinecarboxamide. When the addition was complete, the reaction mixture was stirred at room temperature for 18 hours and then refluxed for two hours. After cooling to room temperature, the mixture was treated dropwise, successively, with 8 mL of water, 8 mL of 15% aqueous sodium hydroxide and 24 mL of water, titrating the final addition to produce a granular precipitate. The solid was removed by filtration, washed with tetrahydrofuran and the filtrate evaporated in vacuo to give 15.6 g of 1-(phenylmethyl)-N-(2-propyl)-3-pyrrolidinemethanamine as a heavy syrup.

This material was used for the next step without further purification.

N-(2-Propyl)-3-pyrrolidinemethanamine

A mixture of 13.4 g (58.0 mmol) of 1-phenylmethyl-N-(2-propyl)-3-pyrrolidinemethanamine, 1.0 g of 20% palladium on carbon and 130 mL of methanol was shaken in an atmosphere of hydrogen at about $4.5 \times 10^5$ Pa at room temperature for 24 hours. The catalyst was removed by filtration through Celite; the filtrate concentrated and distilled in vacuo to give 6.3 g of N-(2-propyl)-3-pyrrolidinemethanamine, bp 58°–60° C./3.5 mm.

Example F 1,1-Dimethylethyl (3-Pyrrolidinyl)carbamate 1,1-Dimethylethyl [1-(Phenylmethyl)-3-pyrrolidinyl]carbamate A solution of 77.0 g (0.44 mole) of 3-amino-1-(phenylmethyl)pyrrolidine [J. Med. Chem , 24, 1229 (1981)], 440 mL (0.44 mole) 1.0N sodium hydroxide and 600 mL of tertiary butyl alcohol was treated dropwise with 98.2 g (0.45 mole) of di-tertiarybutyl dicarbonate. The reaction was stirred at room temperature for 18 hours and the solvent removed in vacuo. The residue was partitioned between ether and water. The aqueous layer was reextracted with ether, the combined ether layers were washed with water, dried (MgSO$_4$), filtered and evaporated on a steam bath replacing the ether with petroleum ether. The crystals which formed were removed by filtration, washed with ether/petroleum ether (1:1), and dried in vacuo to give 84.8 g of 1,1-dimethylethyl [1-(phenylmethyl)-3-pyrrolidinyl]carbamate, mp 114°–115°. A second crop (16.7 g) was obtained by concentrating the filtrate.

1,1-Dimethylethyl (3-Pyrrolidinyl)carbamate

A mixture of 27.6 g (0.1 mole) of 1,1-dimethylethyl[1-(phenylmethyl)-3-pyrrolidinyl]carbamate, 1.0 g of 20% palladium on carbon and 140 mL of methanol was shaken in an atmosphere of hydrogen at about 50 psi and room temperature for 24 hours. The catalyst was removed by filtering through Celite, and the filtrate was concentrated in vacuo to give 18.4 g of 1,1-dimethylethyl (3-pyrrolidinyl)carbamate which solidified upon standing.

Example G

7-Chloro-1-cyclopropyl-6-fluoro-1,4-dihydro-4-oxo-1,8-naphthyridine-3-carboxylic Acid 4-[6-(Cyclopropylamino)-3-nitro-2-pyridinyl]--1-piperazinecarboxylic Acid, Ethyl Ester A solution of 126.0 g (0.4 mole) of 4-(6-chloro-3-nitro-2-pyridinyl)-1-piperazinecarboxylic acid, ethyl ester (prepared as described in European Patent Publication No. 9425), 76.1 g (0.5 mole) of 1,8-diazabicyclo[5.4.0]undec-7-ene (DBU), 28.6 g (0.5 mole) of cyclopropylamine and 500 mL of absolute ethanol was stirred at room temperature for 48 hours. The solution was then heated at reflux for four hours and concentrated in vacuo. The residue was partitioned between chloroform and water. The chloroform layer was dried over magnesium sulfate and concentrated in vacuo. The residue was triturated with ether to give 64.0 g of the title compound, mp 100°–103° C.

4-[6-(Acetylcyclopropylamino)-3-nitro-2-pyridinvl]-1-piperazinecarboxylic Acid, Ethyl Ester A solution of 64.0 g (0.19 mole) of 4-[6-(cyclopropylamino)-3-nitro-2-pyridinyl]-1 -piperazinecarboxylic acid, ethyl ester, 115 mL of acetic anhydride and 115 mL of acetic acid was heated on a steam bath for 36 hours. The solvents were removed in vacuo, the residue was triturated with a mixture of ethanol and toluene which was also evaporated in vacuo to give 68.3 g of the title compound, mp 90°–93° C.

4-[6(Acetylcyclopropylamino)-3-amino-2-pyridinyl]-1-piperazinecarboxylic Acid, Ethyl Ester A mixture of 17.0 g (45 mmole) of 4-[6-(acetylcyclopropylamino)-3-nitro-2-pyridinyl-1-piperazine-carboxylic acid, ethyl ester, 1.5 g of Raney nickel and 180 mL of absolute ethanol was shaken in a atmosphere of hydrogen at about 50 psi and room temperature for approximately 24 hours. The catalyst was removed by filtering through Celite and the solvent removed in vacuo to give 15.2 g of the title compound, mp 149°-150° C.

2-[4-(Ethoxycarbonyl)-1-piperazinyl]-6-(acetylcyclopropylamino)-3-pyridinediazonium Tetrafluoroborate A solution of 20.8 g (60 mmole) of 4-(6-acetylcyclopropylamino)-3-amino-2-pyridinyl]-1-piperazinecarboxylic acid, ethyl ester, 44 mL of ethanol and 27 mL of 48% tetrafluoroboric acid was cooled to 0° C. and treated dropwise with a solution of 4.56 g (66 mmol) of sodium nitrite in 87 mL of water under a nitrogen atmosphere keeping the temperature 0°-5° C. After the addition was complete, the reaction was stirred at 0°-5° C. for one hour and treated with 150 mL of anhydrous ether keeping the temperature below 10° C. The solid was removed by filtration, the precipitate was washed with ethanol/ether (1:1), ether and dried in vacuo to give 24.5 g of the title compound, mp 100°-105° C. (dec.).

4-[6-(Acetylcyclopropylamino)-3-fluoro-2-pyridinyl]-1-piperazinecarboxylic Acid, Ethyl Ester To 800 mL of refluxing toluene was added in portions, as a solid, 46.2 g (0.1 mole) of 2-[4-(ethoxycarbonyl)-1-piperazinyl]-6-(acetylcyclopropylamino)-3-pyridinediazonium tetrafluoroborate. After the addition was complete, the reaction was refluxed for ten minutes and the toluene was decanted from the insoluble precipitate. The toluene was evaporated in vacuo and the residue was partitioned between chloroform and water. The chloroform layer was washed with 5% aqueous sodium bicarbonate, water, dried over magnesium sulfate and evaporated in vacuo to give 13.7 g of the title compound, as a viscous oil. An additional 10.2 g could be obtained by partitioning the original toluene insoluble material in chloroform and water. The organic layer was washed with 5% aqueous sodium bicarbonate, dried over magnesium sulfate, evaporated in vacuo and the residue was chromatographed on silica gel eluting with chloroform/ethyl acetate (6:4). This fraction was also a viscous oil which did not crystallize upon standing. Both fractions were of sufficient purity to be used as is in the ensuing steps.

4-6-(Cyclopropylamino)-3-fluoro-2-pyridinyl]-1-piperazinecarboxylic Acid, Ethyl Ester A solution of 21.9 g (63 mmole) of 4-[6-(acetylcyclopropylamino)-3-fluoro-2-pyridinyl]-1-piperazine-carboxylic acid, ethyl ester, 170 mL of 15% hydrochloric acid and 235 mL of methanol was refluxed for one hour and allowed to stir at room temperature for 18 hours The methanol was removed in vacuo and the aqueous acid was made basic with 1.0N sodium hydroxide to pH 10.5. The mixture was extracted with chloroform, the chloroform layer washed with water, dried over magnesium sulfate, and evaporated in vacuo to give 17.6 g of the title compound, mp 68°-70° C.

1-Cyclopropyl-6-fluoro-1,4-dihydro-4-oxo-7-(1-piperazinyl)-1,8-naphthyridine-3-carboxylic Acid

Route A

1-[Cyclopropyl[6-[4-(ethoxycarbonyl)-1-piperazinyl]-5-fluoro-2-pyridinyl]amino]methylene ]propanedioic Acid, Diethyl Ester A solution of 3.8 g (12.3 mmole) of 4-[6-(cyclopropylamino)-3-fluoro-2-pyridinyl]-1-piperazine-carboxylic acid, ethyl ester, 2.7 g (12.3 mmole) of diethyl (ethoxymethylene)malonate and 50 mL of xylene was refluxed for 24 hours. The solvent was removed in vacuo and the residue was chromatographed over silica gel eluting with chloroform/ethyl acetate (80/20) to give 2.3 g of the title compound as a viscous oil which was used without further purification.

Ethyl 1-Cyclopropyl-6-fluoro-1,4-dihydro-4-oxo-7-[4-(ethoxycarbonyl)-1-piperazinyl]-1,8-naphthyridine-3-carboxylate A solution of 2.3 g (4.8 mmole) of [[cyclopropyl[6-[4-(ethoxycarbonyl)-1-piperazinyl]-5-fluoro-2-pyridinyl]amino]methylene]propanedioic acid, diethyl ester, in 15 mL of acetic anhydride was treated dropwise with 5 mL of 98% sulfuric acid keeping the temperature 55°-60° C. When the addition was complete, the reaction was stirred for one hour and poured onto 50 g of ice. The aqueous suspension was extracted with chloroform, the chloroform layer washed with water, dried over magnesium sulfate, filtered, and evaporated in vacuo. The residue was triturated with several portions of ethanol/toluene which were also removed in vacuo to give 0.4 g of the title compound, mp 184°-186° C. An additional 0.5 g of product could be obtained by concentrating the original aqueous fraction, mp 184°-186° C.

1-Cyclopropyl-6-fluoro-1,4-dihydro-4-oxo-7-(1-piperazinyl)-1,8-naphthyridine-3-carboxylic Acid A suspension of 0.7 g (1.6 mmole) of ethyl 1-cyclopropyl-6-fluoro-1,4-dihydro-4-oxo-7-[4-(ethoxycarbonyl)-1-piperazinyl]-1,8-naphthyridine-3-carboxylate, 6 mL of 10% aqueous sodium hydroxide and 2 mL of ethanol was refluxed for three hours. The reaction was filtered through a fiber glass pad to clarify and acidified to pH 1.5 with 6.0M hydrochloric acid and lyophilized. The residue was dissolved in 10 mL of ammonium hydroxide and the solution concentrated in vacuo. The precipitate which formed was removed by filtration, washed with aqueous ethanol, ether and dried in vacuo to give 0.04 g, mp 274°-276° C.

Route B

4-[6-Cyclopropyl(2,2-dimethyl-4,6-dioxo-1,3-dioxan-5-ylidine)amino]-3-fluoro-2-pyridinyl ]-1-piperazine-carboxylic Acid, Ethyl Ester A solution of 17.6 g (57 mmole) of 4-[6-(cyclopropylamino)-3-fluoro-2-pyridinyl]-1-piperazine-carboxylic acid, ethyl ester, 11.6 g (63 mmole) of 5-methoxymethylene)-2,2-dimethyl-1,3-dioxane-4,4-dione and 250 mL of methanol was stirred at room temperature for four hours. The solid was removed by filtration, washed with methanol, ether and dried in vacuo to give 17.6 g of the title compound, mp 177°-178° C.

1-Cyclopropyl-6-fluoro-1,4-dihydro-4-oxo-7-[4-(ethoxycarbonyl)-1-piperazinyl]-3 -carboxylic Acid A solution of 17.0 g (37.0 mmole) of 4-[6-(cyclopropyl(2,2-dimethyl-4,6-dioxo-1,3-dioxan-5-ylidene)amino]-3-fluoro-2-pyridinyl]-1-piperazinecarboxylic acid, ethyl ester in 125 mL of acetic anhydride was treated dropwise with 35 mL of 98% sulfuric acid keeping the temperature 50°-60° C. When the addition was complete, the reaction was stirred for two hours and poured onto 600 g of ice. The mixture was stirred for one hour and the resulting precipitate was removed by filtration, washed with water and dried in vacuo to give 10.2 g of the title compound, mp 277°-279° C.

1-Cyclopropyl-6-fluoro-1,4-dihydro-4-oxo-7-(1-piperazinyl)-1,8-naphthyridine-3-carboxylic Acid A solution of 10.2 g (25 mmole) of 1-cyclopropyl-6-fluoro-1,4-dihydro-4-oxo-7-[4-( ethoxycarbonyl)-1-piperazinyl]-1,8-naphthyridine-3-carboxylic acid, 100 mL of 10% aqueous sodium hydroxide and 40 mL of ethanol was refluxed for three hours. The solution was concentrated to 125 mL and acidified to pH 7.3 with glacial acetic acid. The resulting precipitate was removed by filtration, washed with 50% aqueous ethanol, ether and dried in vacuo to give 7.2 g of the title compound, mp 274°-276°.

1-Cyclopropyl-6-fluoro-1,4-dihydro-7-hydroxy-4-oxo-1,8-naphthyridine-3-carboxylic Acid To a solution of 2 mL of 70% nitric acid in 10 mL of 98% sulfuric acid was added in portions 1.0 g (3.0 mmole) of 1-cyclopropyl-6-fluoro-1,4-dihydro-4-oxo-7-(1-piperazinyl)-1,8-naphthyridine-3 -carboxylic acid, keeping the temperature between 25°-30° C. The resulting solution was stirred at room temperature for 18 hours and poured onto 40 g of ice. The mixture was stirred at room temperature for 24 hours, concentrated in vacuo, the pH adjusted to 12 with aqueous sodium hydroxide, and filtered through a fiber glass pad. The filtrate was acidified to pH 3.5 with 6.0M hydrochloric acid, the resulting precipitate removed by filtration, washed with water then ether and dried in vacuo to give 0.23 g of the title compound, mp 325°-327° C.

7-Chloro-1-cyclopropyl-6-fluoro-1,4-dihydro-4-oxo-1,8-naphthyridine-3-carboxylic Acid A suspension of 0.19 g (0.72 mmole) of 1-cyclopropyl-6-fluoro-1,4-dihydro-7-hydroxy-4-oxo-1,8 -naphthyridine-3-carboxylic acid in 2 mL of phosphorus oxychloride was heated at reflux for ½ hour. The resulting solution was cooled to room temperature and the solvent was removed in vacuo. The residue was triturated with ice-water and the resulting solid was removed by filtration, washed with water, then ether and dried in vacuo to give 0.11 g of the title compound, mp 209°-212° C.

Example H

(S)-N-Ethyl-3-pyrrolidinemethanamine Dihydrochloride

[3R-(R*,R*)]and [3S-(R*,S*)]-5-Oxo-1-(1-phenylethyl)-3-pyrrolidinecarboxylic Acid A mixture of 13.10 g (0.1 mole) itaconic acid and 12.12 g (0.1 mole) R(+)-α-methylbenzylamine in 100 mL xylene was refluxed overnight, cooled to room temperature, and filtered to afford 14.76 g (63%) of colorless crystals of the title compound as a mixture of diastereomers; $[\alpha]_D + 113.6°$ C. (C, 1.16, ethanol).

Anal calcd. for $C_{13}H_{15}NO_3$;
C, 66.93; H, 6.48; N, 6.00.
Found C, 67.30; H, 6.24; N, 5.92.

[3R-(R*,R*)] and [3S-(R*,S*)]-5-oxo-1-(1-phenylethyl)-3-pyrrolidinecarboxylic Acid, Methyl Ester A solution of 126 6 g (0.543 mole) [3R-(R*,R*)]-and [3S-(R*,S*)]-5-oxo-1-(1-phenylethyl)-3-pyrrolidine-carboxylic acid and 0.50 g p-toluenesulfonic acid in 1300 mL methanol was refluxed overnight. The solvent was evaporated and the residue taken up in dichloromethane, washed with 3×300 mL 1N NaOH solution, dried (MgSO₄) and evaporated to afford 131.7 g of a mixture of diastereomeric esters. Chromatography on a column of silica gel with ethyl acetate-pentane (3:2) afforded 74.9 g (56%) of [3R-(R*,R*)]-5-oxo-1-(1-phenylethyl)-3-pyrrolidinecarboxylic acid, methyl ester as a liquid, $[\alpha]_D + 84.1°$ (C, 1.06 methanol).

Anal. calcd. for $C_{14}H_{17}NO_3$:
C, 68.00; H, 6.93; N, 5.66.
Found C, 67.74; H, 7.27; N 5.48.

Evaporation of later fractions afforded 38.3 g (29%) of [3S-(R*,S*)-5-oxo-1-(1-phenylethyl)-3-pyrrolidinecarboxylic acid, methyl ester as colorless crystals, mp 69°-71° C., $[\alpha]_D + 116.2°$ C. (C, 1.03, methanol).

Anal. calcd. for $C_{14}H_{17}NO_3$;
Found: C, 68.00; H, 6.93; N, 5.66.
C, 66.69; H, 6.94; N, 5.34.

[3R-[R*,R*)]-1-(1-Phenylethyl)-3-pyrrolidinemethanol

A solution of 10.0 g (40.5 mmol) [3R-(R*, R*)]-5-oxo-1-(-1-phenylethyl)-3 -pyrrolidinecarboxylic acid, methyl ester in 75 mL dry tetrahydrofuran was added dropwise to a mixture of 6.50 g (171 mmol) of lithium aluminum hydride in 100 mL of tetrahydrofuran. The mixture was refluxed overnight, diluted with 50 mL of tetrahydrofuran and treated dropwise successively with 6.5 mL water, 6.5 mL 15% sodium hydroxide and 19.5 mL water. Solids were removed by filtration and the filtrate was evaporated to a syrup which was dissolved in dichloromethane, dried (MgSO₄), and reevaporated to give 8.06 g of crude crystalline product. Recrystallization from hexane afforded 7.25 g (87%) of the title compound, mp 86°-88° C. $[\alpha]_D + 51.3°$ C. (C, 1.06, methanol).

Anal. calcd. for $C_{13}H_{19}NO$:
Found: C, 76.06; H, 9.33; N, 6.82.
C, 76.38; H, 9.63; N, 7.05.

[3R-(R*,R*)]-3-Chloromethyl-1-(1-phenylethyl)pyrrolidine

A solution of 0.50 g (2.44 mmol) [3R-(R*,R*)]-(1-phenylethyl)-3-pyrrolidinemethanol in 5 mL 1,2-dichloroethane was treated with 2 mL thionyl chloride, refluxed two hours, evaporated, and crystallized by trituration with ether to afford 0.64 g (100%) of the title compound as the hydrochloride, mp 140°-146° C., $[\alpha]_D + 27.8°$ C. (c, 1.07, methanol).

Anal. calcd. for $C_{13}H_{19}C_{12}N$;
C, 60.00; H, 7.36; N, 5.38; Cl, 27.25.
Found: C, 59.75; H, 7.09; N, 5.25; Cl, 26.94.

[3S-(R*,S*)]-N-Ethyl-1-(1-phenylethyl)-3-pyrrolidinemethanamine

A solution of 4.0 g (15.4 mmol) [3R-(R*,R*)]-3-(chloromethyl)-1-(1-phenylethyl)pyrrolidine in 60 mL 70% ethylamine was heated in a pressure bottle on the steam bath overnight. The mixture was cooled, filtered, and evaporated to a thick syrup which was treated with 50 mL 2N sodium hydroxide and extracted with 3×30 mL dichloromethane. The combined organic layer was dried (MgSO$_4$) and evaporated to afford 3.49 g (98%) of the title compound as a syrup, $[\alpha]_D$+45.6° C. (C, 1.04, methanol).

Anal. calcd. for C$_{15}$H$_{24}$N$_2$:
C, 77.53; H, 10.41; N, 12.06.
Found: C, 77.14; H, 10.23; N, 11.91.

(S)-N-Ethyl-3-pyrrolidinemethanamine Dihydrochloride

A solution of 5.97 g (25.7 mmol) [3S-(R*,S*)]-N-ethyl-1-(1-phenylethyl)-3-pyrrolidinemethanamine in 100 mL methanol with 0.6 g 20% PD/C catalyst was hydrogenated at 50 psi for 23 hours. More catalyst (0.6 g) was added and the reaction continued an additional 23 hours. After filtration and evaporation of solvent the product was distilled to afford 2.05 g (62%) of the title compound as the free base, bp 74° C. (8 mm Hg). A sample (0.25 g) dissolved in 10 mL ether was treated with 1 mL 6N hydrogen chloride in 2-propanol to afford 0.29 g of the amine dihydrochloride after two crystallizations from ethanol, mp 184.5°-185.5° C., $[\alpha]_D$+5.4° C. (C, 0.85, 0.1N NaOH).

Example I

N,N-Dimethyl-3-pyrrolidinemethanamine

N,N-Dimethyl-5-oxo-1-(phenylmethyl)-3-pyrrolidinecarboxamide

A mixture of 15.0 g (64.3 mmol) of methyl 5-oxo-1-(phenylmethyl)pyrrolidinecarboxylate [J. Org. Chem., 26, 1519 (1961)] and 100 mL of methyl alcohol was cooled to 0° C. for 0.5 hours. To this solution excess N,N-dimethylamine (approximately 50 g, 1.11 mole) was added. The reaction was stirred overnight and brought to room temperature. The mixture was concentrated under reduced pressure and chromatographed over silica using chloroform, hexane, 2-propanol (6:3:1) giving 4.91 g (31%) of N,N-dimethyl-5-oxo-1-(phenylmethyl)-3-pyrrolidinecarboxamide as a clear yellow oil. This material was used in the next step.

N,N-Dimethyl-1-(phenylmethyl)-3-pyrrolidinemethanamine

A solution of 2.91 g (11.8 mmol) N,N-dimethyl-5-oxo-1-(phenylmethyl)-3-pyrrolidinecarboxamide and 15 mL anhydrous tetrahydrofuran was added dropwise into a suspension of 1.41 g (35 mmol) lithium aluminum hydride in 30 mL tetrahydrofuran. The reaction was refluxed overnight then cooled to room temperature. To the solution was added dropwise successively 1.5 mL water, 1.5 mL 15% sodium hydroxide and 4.5 mL of water. The resulting precipitate was filtered. The filtrate was concentrated under reduced pressure, dissolved in dichloromethane, dried over magnesium sulfate and the solvent evaporated under reduced pressure. The residue was bulb to bulb distilled giving 1.5 g (58%) of N,N-dimethyl-1-(phenylmethyl)-3-pyrrolidinemethanamine as a clear liquid. This material was used in the next step.

N,N-Dimethyl-3-pyrrolidinemethanamine

A mixture of 1.25 g (5.72 mmol) of N,N-dimethyl-1-(phenylmethyl)-3-pyrrolidinemethanamine, 100 mL of methyl alcohol, 0.2 g of 20% palladium on carbon and hydrogen were shaken at a pressure of 55.1 psi. After 16.8 hours the catalyst was filtered and the filtrate evaporated under reduced pressure. The residue was bulb to bulb distilled yielding 0.71 g (97%) N,N-dimethyl-3-pyrrolidinemethanamine as a clear yellow oil.

Example J

N,N-Diethyl-3-pyrrolidinemethanamine

N,N-Diethyl-1-(phenylmethyl)-3-pyrrolidinemethanamine

To a solution of 32.9 g (0.15 mole) 5-oxo-1-(phenylmethyl)-3-pyrrolidinecarboxylic acid [J. Org. Chem., 26, 1519 (1961)] and 300 mL of dichloromethane was added 15.2 g (0.15 mole) of N-methylmorpholine. After 15 minutes the solution was cooled to −25° C. and 16.3 g (0.15 mole) of ethyl chloroformate was added. After an additional ten minutes, a solution of 13.5 g (0.18 mole) of diethylamine and 18 mL dichloromethane was added to the reaction. Carbon dioxide was evolved and after 1.5 h another 10 g (0.13 mole) of diethylamine in 10 mL of dichloromethane was added. The reaction was stirred four hours, washed with 1N sodium hydroxide, dried over magnesium sulfate, and concentrated under reduced pressure. The residue was added to a suspension of 17.4 g (0.46 mole) of lithium aluminum hydride and 210 mL anhydrous tetrahydrofuran. The reaction was refluxed overnight then cooled to room temperature. The cooled solution was quenched by the successive addition of 17.4 mL water, 17.4 mL 15% sodium hydroxide, and 52.2 mL water. The resulting precipitate was filtered and washed with ethyl alcohol. The filtrate was concentrated under reduced pressure, taken up in dichloromethane and dried over magnesium sulfate. The solvent was removed under vacuum giving 25.8 g (69%) of N,N-diethyl-1-(phenylmethyl)-3-pyrrolidinemethanamine as a yellow oil. This material was used in the next step without purification.

N,N-Diethyl-3-pyrrolidinemethanamine

A mixture of 25.4 g (0.10 mole) of N,N-diethyl-1-(phenylmethyl)-3-pyrrolidinemethanamine, 200 mL of methyl alcohol, 2 g of palladium on carbon and hydrogen were shaken at a pressure of 51.5 psi. After 20.3 hours, the catalyst was filtered and the filtrate concentrated under reduced pressure. The residue was bulb to bulb distilled giving 15.9 g of N,N-diethyl-3-pyrrolidinemethanamine.

Example K

3-(Ethylamino)pyrrolidine

To 12.7 g (72 mmol) of the 3-amino-1-(phenylmethyl)pyrrolidine in 25 mL of acetic acid was added 75 mL of acetic anhydride and the mixture refluxed for four hours. The reaction was concentrated, taken into water, and extracted with ether at pH 11. The ether was dried (magnesium sulfate) and concentrated to give 10.93 g of an oil. This material was taken directly into dry tetrahydrofuran and added dropwise to 7.0 g (184 mmol) of lithium aluminum hydride in 75 mL of tetrahydrofuran at 10° C. The mixture was refluxed for 18 hours, cooled to room temperature, and then treated sequentially with 7.0 mL of water, 7.0 mL of 15% sodium hydroxide, and 21.0 mL of water. The mixture was filtered, concentrated, taken up in dichloromethane, dried (magnesium sulfate), concentrated, and distilled in vacuo to give 8.30 g of 3-(ethylamino)-1-(phenylmethyl)pyrrolidine. This product was treated with 1.0 g of 20% palladium on charcoal in 100 mL of methanol and hydrogenated at 541.4 psi. After 24 hours, the mixture was filtered, concentrated, and distilled to give 2.1 g of 3-(ethylamino)pyrrolidine.

Example L 3-(1-N-tert-butoxycarbonylamino)ethyl)pyrrolidine (Isomer A)

3-(1-Benzyl-2-oxopyrrolidin-4-yl)-3-oxopropanoate 1,1'-Carbonyldiimidazole (42.5 g, 0.262 mole) was added to a stirred solution of 1-benzyl-2-oxopyrrolidine-4-carboxylic acid (50.0 g, 0.228 mole) in dry tetrahydrofuran (550 mL) under nitrogen in five portions over 30 minutes (gas evolution). The mixture was warmed at 45° for 16 hours. Magnesium bis-(ethylmalonate) (81.0 g, 0.283 mole) was added (vigorous gas evolution!). The reaction was heated at reflux three hours and cooled to room temperature. The solvent was removed under reduced pressure to give a foam which was dissolved in dichloromethane, washed with 1N HCl (600 mL), water (600 mL), dilute sodium bicarbonate (600 mL), and dried (MgSO$_4$). The solvent was removed under reduced pressure to give 3-(1-benzyl-2-oxopyrrolidin-4-yl)-3-oxopropanoate (58.2 g, 88%) as an orange oil.

NMR δ (CDCl$_3$) 7.1 (5H,m), 4.31 (2H,d), 4.05 (2H,q), 3.38 (4H,m), 2.42-2.67 (2H,m), 1.20 (3H,t).

4-Acetyl-1-benzyl-2-pyrrolidinone

A mixture of 3-(1-benzyl-2-oxopyrrolidin-4-yl)-3-oxopropanoate (24.0 g, 0.083 mole) and sodium chloride (10.6 g, 0.181 mole) in dimethylsulfoxide (105 mL)/water (4.4 mL) was heated at 135° with stirring for 16 hours. On cooling the reaction mixture was poured onto ice water (900 mL) and extracted with dichloromethane (800 mL). The organic phase was washed with water (4×500 mL) and dried (MgSO$_4$). The solvent was removed under reduced pressure to give 4-acetyl-1-benzyl-2-pyrrolidinone (15.0 g, 83%) as a brown oil.

NMR δ (CDCl$_3$) 7.02-7.32 (5H,m), 4.03 (2H,d), 3.05-3.42 (3H,m), 2.50-2.70 (2H,m) 2.21 (3H,s).

1-Benzyl-4-(1-hydroxyiminoethyl)-2-oxopyrrolidine

Hydroxylamine hydrochloride (5.58 g, 0.076 mole) was added to a solution of 4-acetyl-1-benzyl-2-pyrrolidinone (15.0 g, 0.069 mole) in pyridine (250 mL) and the reaction mixture was heated at 40° with stirring under nitrogen for 18 hours. The solvent was removed under reduced pressure at 65° and the residue was dissolved in chloroform (900 mL), washed with water (500 mL), 0.5M HCl (3×500 mL), and dried (MgSO$_4$). The solvent was removed under reduced pressure to give 1-benzyl-4-(1-hydroxyiminoethyl)-2-oxo-pyrrolidine (16.7 g, quant) as a brown solid.

NMR (CDCl$_3$) 7.5 (5H,m), 4.32 (2H,d), 2.82-3.40 (3H,m), 2.46-2.64 (2H,m), 1.77 (3H,s).

4-(1-Aminoethyl)-1-benzyl-2-oxopyrrolidine

1-Benzyl-4-(1-hydroxyiminoethyl)-2-oxopyrrolidine (16.81 g, 0.072 mole), was hydrogenated in saturated methanolic ammonia (200 mL) at 50 psi and 25° with Raney nickel (5 g) for 23 hours. Additional Raney nickel (5 g) was added and hydrogenation continued for three hours. The reaction was Celite filtered and the solvent was removed under reduced pressure to give 4-(1-aminoethyl)-1-benzyl-2-oxopyrrolidine (14.4 g, 91%) as a brown oil which solidified on standing to a brown solid.

NMR δ (CDCl$_3$) 7.15 (5H, broad s), 4.30 (2H, broad s), 2.05-3.39 (11H,m) 0.91-1.15 (3H,m).

Example M

Separation of Diastereomers of 4-(1-aminoethyl)-1-benzyl-2-oxopyrrolidine 4-(1-Aminoethyl)-1-benzyl-2-oxopyrrolidine (4.0 g, 0.018 mole) was flash chromatographed on silica gel (840 g) eluting with 73/1/1 chloroform/triethylamine/ethanol to obtain isomer A followed by elution with 38/1/1 chloroform/triethlamine/ethanol to obtain isomer B. The solvent was removed under reduced pressure to give isomer A (1.5 g, 38%) as a pale gold oil and isomer b (1.6 g, 40%) as an off-white solid.

NMR δ (CDCl$_3$) isomer A: 7.25-7.34 (5H,m), 4.44 (2H,d), 3.33-3.42 (1H,m), 3.05-3.14 (1H,m), 2.78-2.88 (1H,m), 2.44-2.54 (1H,m), 2.18-2.30 (5H,m), 1.07 (3H,d).

NMR δ (CDCl$_3$) isomer B: 7.21-7.35 (5H,m) 4.44 (2H,d), 3.24-3.33 (1H,m), 2.91-3.05 (5H,m), 2.55-2.65 (1H,m), 2.24-2.42 (2H,m), 1.05 (3H,m).

Example N 3-(1-Aminoethyl)-1-benzylpyrrolidine (Isomer A)

Lithium aluminum hydride (0.55 g, 0.014 mole) was added to tetrahydrofuran (45 mL) with stirring under nitrogen. 4-(1-Aminoethyl)-1-benzyl-2-oxopyrrolidine (1.60 g, 0.0073 mole) was added in several portions over 30 minutes and the reaction was brought to reflux over 75 minutes. The reaction was refluxed 16 hours and cooled to room temperature. The reaction was treated with water (0.55 mL), 10% NaOH (0.55 mL), and water (1.65 mL) slowly dropwise and the solid filtered off and washed with dichloromethane. The combined filtrates were evaporated under reduced pressure to give 3-(1-aminoethyl)-1-benzylpyrrolidine isomer A (1.05 g, 70%) as a yellow oil.

NMR δ (CDCl$_3$) 7.22-7.34 (5H,m), 3.59 (2H,d), 2.39-2.84 (5H,m), 1.87-2.19 (4H,m), 1.48-1.7 (5H,m), 1.00 (3H,d).

1-Benzyl-3-(1-N-(tert-butoxycarbonylamino)ethyl)pyrrolidine (Isomer A)

Di-tert-butyldicarbonate (1.97 g, 0.0089 mole) was added to 3-(1-aminoethyl-1-benzylpyrrolidine isomer A (1.78 g, 0.0087 mole) in 1N NaOH (9 mL)/tert-butanol (12 mL) and the reaction was stirred at room temperature 16 hours. A precipitate was observed almost immediately. The solvent was removed under reduced pressure and the residue was partitioned between diethyl ether and water. The layers were separated and the aqueous layer was extracted with diethyl ether. The organic layers were combined and dried (MgSO$_4$). The solvent was removed under reduced pressure to give 1-benzyl-3-(tert-butoxycarbonylaminoethyl)pyrrolidine isomer A (2.02 g, 77%) as a pale yellow oil.

NMR δ (CDCl₃) 7.24–7.36 (5H,m), 5.55 (1H,m), 3.49–3.70 (2H,m), 2.32–2.74 (4H,m), 1.48–2.18 (4H,m), 1.46 (9H,s), 1.13 (3H,d).

3-(1-(N-tert-butoxycarbonylamino)ethyl)pyrrolidine (Isomer A)

1-Benzyl-3-(1-N-tert-butoxycarbonylamino)ethyl)-pyrrolidine isomer A (2.01 g, 0.01 mole) was debenzylated in methanol (100 mL) at 50 PSI and 25° with palladium/carbon (0.5 g) for 18 hours. Additional palladium/carbon (0.5 g) was added and the reaction continued for three hours. The reaction was Celite filtered and the solvent was removed under reduced pressure to give 3-(1-N-tert-butoxycarbonylamino)ethyl)pyrrolidine isomer A (1.55 g, quant) as a colorless oil.

NMR δ (CDCl₃) 4.63–4.67 (1H,m), 2.88–3.08 (3H,m), 2.68–2.81 (4H,m), 1.85–2.07 (2H,m), 1.41–1.53 (12H,m), 1.15 (3H,d).

Example Q 3-(1-Aminoethyl)-1-benzylpyrrolidine (Isomer B)

Lithium aluminum hydride (0.52 g, 0.014 mole) was added to tetrahydrofuran (40 mL) with stirring under nitrogen. 4-(aminoethyl)-1-benzyl-2-oxopyrrolidine (1.50 g, 0.0069 mole) was added in several portions over 30 minutes and the reaction brought to reflux over 75 minutes. The reaction was refluxed 16 hours and cooled to room temperature. The reaction was treated dropwise successively with water (0.5 mL), 10% NaOH (0.5 mL), water (1.5mL) and the solid filtered off and washed with dichloromethane. The combined filtrates were evaporated under reduced pressure to give 3-(1-aminoethyl)-1-benzylpyrrolidine isomer B (1.03 g, 73%) as a yellow oil.

NMR δ (CDCl₃) 7.20–7.36 (5H,m), 3.60 (2H,s), 2.62–2.83 (3H,m), 2.37–2.57 (1H,m), 2.22–2.30 (1H,m), 1.83–2.08 (2H,m), 1.38–1.67 (4H,m), 1.05 (3H,d).

1-Benzyl-3-(1-(N-tert-butoxycarbonylamino)ethyl)pyrrolidine (Isomer B)

Di-tert-butyldicarbonate (2.27 g, 0.0102 mole) was added to 3-(1-aminoethyl)-1-benzylpyrrolidine isomer B (2.05 g, 0.01 mole) in 1H NaOH (10 mL)/tert-butanol (14 mL) and the reaction was stirred at room temperature 16 hours. A precipitate was observed after one hour. The solvent was removed under reduced pressure and the residue was partitioned between diethyl ether and water. The layers were separated and the aqueous layer was extracted with diethyl ether. The organic layers were combined and dried (MgSO₄). The solvent was removed under reduced pressure to give 3-(1-N-tert-butoxycarbonylamino)ethyl)pyrrolidine isomer B (1.95 g, 64%) as a pale yellow oil.

NMR δ (CDCl₃) 7.20–7.36 (5H,m), 3.47–3.67 (3H,m), 2.51–2.62 (3H,m), 2.10–2.30 (2H,m), 1.50–1.99 (3H,m), 1.46 (9H,s), 1.09 (3H,d).

3-(1-N-tert-butoxycarbonylamino)ethyl)pyrrolidine (Isomer B)

1-Benzyl-3-(1-N-tert-butoxycarbonylamino)ethyl)-pyrrolidine isomer B (1.89 g, 0.0062 mole) was debenzylated in methanol (100 ml) at 50 psi and 25° with palladium/carbon (0.5 g) for 20 hours. The reaction was Celite filtered and the solvent was removed under reduced pressure to give 3-(1-(N-tert-butoxycarbonylamino)ethyl)pyrrolidine isomer B (1.42 g, quant) as a colorless oil.

NMR δ (CDCl₃) 2.88–3.08 (3H,m), 2.53–2.62 (1H,m), 2.32 (2H, broad s), 1.84–2.05 (2H,m), 1.44 (10H,s), 1.12 (3H,d).

What is claimed is:

1. A compound of the formula

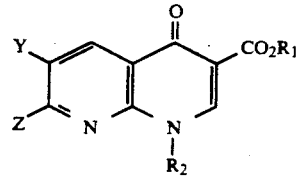

wherein Z is —Z'~(CR₅R₆)$_{n''}$NR₃R₄, in which Z' is

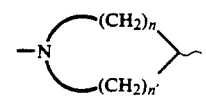

Y is hydrogen, fluorine, chlorine, or bromine;

n is 1, 2, 3, or 4, n' is 1, 2, 3, or 4 wherein n+n' is a total of 2,3,4, or 5;

n" is 1 or 2;

R₁ is hydrogen, alkyl having from one to six carbon atoms or a cation;

R₂ is alkyl having from one to four carbon atoms or hydroxyalkyl having from two to four carbon atoms or cycloalkyl having three to six carbon atoms;

R₃ is hydrogen, alkyl having from one to four carbon atoms or cycloalkyl having three to six carbon atoms;

R₄ is hydrogen, alkyl from one to four carbon atoms, hydroxyalkyl having two to four carbon atoms, trifluoroethyl or R₇CO— wherein R₇ is alkyl having from one to four carbon atoms, or alkoxy having from one to four carbon atoms;

R₅ is hydrogen, or alkyl having from one to three carbon atoms;

R₆ is hydrogen or alkyl having from one to three carbon atoms, or a pharmaceutically acceptable acid addition or base salt thereof.

2. A compound as claimed in claim 1, wherein Y is fluorine.

3. A compound as claimed in claim 2, wherein R₂ is ethyl, or cyclopropyl.

4. A compound as claimed in claim 3, wherein R₁ is hydrogen or a pharmaceutically acceptable base salt thereof.

5. A compound as claimed in claim 4, wherein Z is

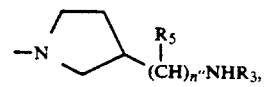

in which n" is 1; R₅ is hydrogen or methyl, and R₃ is hydrogen, methyl, ethyl, 1- or 2-propyl.

6. A compound as claimed in claim 5 and being 7-[3-(aminoethyl)-1-pyrrolidinyl]-1-ethyl-6-fluoro-1,4-dihydro-4-oxo-1,8-naphthyridine-3-carboxylic acid.

7. A compound as claimed in claim 5 and being 1-ethyl-6-fluoro-1,4-dihydro-7-[3-[(methylamino)methyl]-1-pyrrolidinyl]-4-oxo-1,8-naphthyridine-3-carboxylic acid.

8. A compound as claimed in claim 5 and being 1-ethyl-7-[3-[(ethylamino)methyl]-1-pyrrolidinyl]-6-fluoro-1,4-dihydro-4-oxo-1,8-naphthyridine-3-carboxylic acid.

9. A compound as claimed in claim 5 and being 7-[3-(aminoethyl)-1-pyrrolidinyl]-1-cyclopropyl--1,4-dihydro-6-fluoro-4-oxo-1,8-naphthyridine-3-carboxylic acid.

10. A compound as claimed in claim 5 and being 1-cyclopropyl-7-[3-[(ethylamino)methyl]-1-pyrrolidinyl]-1,4-dihydro-6-fluoro-4-oxo-1,8-naphthyridine-3-carboxylic acid.

11. A compound as claimed in claim 5 and being 7-[3-(2-propylamino)methyl]-1-pyrrolidinyl]-1-cyclopropyl-6-fluoro-1,4-dihydro-4-oxo-1,8-naphthyridine-3-carboxylic acid.

12. A compound as claimed in claim 5 and being 7-[3-(propylamino)methyl]-1-pyrrolidinyl]-1-cyclopropyl-6-fluoro-1,4-dihydro-4-oxo-1,8-naphthyridine-3-carboxylic acid.

13. A compound as claimed in claim 5 and being 1-cyclopropyl-6-fluoro-1,4-dihydro-7-[3-[(methylamino)methyl]-1-pyrrolidinyl]-4-oxo-1,8-naphthyridine-3-carboxylic acid.

14. A compound as claimed in claim 5 and being 7-[3-(1-aminoethyl)-1-pyrrolidinyl]-1-cyclopropyl-6-fluoro-1,4-dihydro-4-oxo-1,8-naphthyridine-3-carboxylic acid and its individual epimeric forms.

15. A pharmaceutical composition comprising an antibacterially effective amount of a compound as claimed in claim 1 together with a pharmaceutically acceptable carrier.

16. The method of treating bacterial infections in mammals which comprises administering to said mammal a pharmaceutical composition as claimed in claim 15.

* * * * *

UNITED STATES PATENT AND TRADEMARK OFFICE
CERTIFICATE OF CORRECTION

PATENT NO. : 5,281,612
DATED : Jan. 25, 1994
INVENTOR(S) : Domagala, et al.

It is certified that error appears in the above-indentified patent and that said Letters Patent is hereby corrected as shown below:

Column 31, line 6, delete "(aminoethyl)" and insert instead "(aminomethyl)".

Column 31, line 6, delete last hyphen.

Column 31, line 7, delete hyphen at beginning of line.

Signed and Sealed this

Fifth Day of July, 1994

BRUCE LEHMAN

Attest:

Attesting Officer

Commissioner of Patents and Trademarks